United States Patent
Osadchy et al.

(10) Patent No.: US 6,385,476 B1
(45) Date of Patent: May 7, 2002

(54) METHOD AND APPARATUS FOR INTRACARDIALLY SURVEYING A CONDITION OF A CHAMBER OF A HEART

(75) Inventors: Margarita Osadchy; Daniel Reisfeld, both of Haifa (IL)

(73) Assignee: Biosense, Inc., New Brunswick, NJ (US)

( * ) Notice: Subject to any disclaimer, the term of this patent is extended or adjusted under 35 U.S.C. 154(b) by 0 days.

(21) Appl. No.: 09/399,477

(22) Filed: Sep. 21, 1999

(51) Int. Cl.$^7$ ............................................... A61B 8/05
(52) U.S. Cl. ..................... 600/407; 600/424; 600/425; 600/429; 600/481; 600/483; 600/508; 378/4; 378/6; 378/19; 378/21; 378/42; 378/62; 378/68; 382/131; 382/173; 382/179
(58) Field of Search ............................... 600/407, 310, 600/342, 377, 374, 424, 425, 429, 437, 439, 450, 463, 466, 467, 478, 479, 481, 483, 500, 312; 606/130; 378/4, 6, 14, 21, 42, 62, 68; 382/131, 173, 174

(56) References Cited

U.S. PATENT DOCUMENTS

| | | | |
|---|---|---|---|
| 3,316,896 A | 5/1967 | Thomasset | |
| 4,157,572 A | 6/1979 | Kennedy et al. | 360/33 |
| 4,459,990 A | 7/1984 | Barnea | 128/656 |

(List continued on next page.)

FOREIGN PATENT DOCUMENTS

| | | |
|---|---|---|
| EP | 501993 | 6/1997 |
| EP | 0829228 A1 | 3/1998 |
| EP | 974936 | 1/2000 |
| WO | WO 94/04938 | 3/1994 |
| WO | WO 94/06349 | 3/1994 |
| WO | WO 96/05768 | 2/1996 |
| WO | WO 97/24983 | 6/1997 |
| WO | WO 97/24981 A3 | 7/1997 |
| WO | WO 97/24981 A2 | 7/1997 |
| WO | WO 97/25101 | 7/1997 |
| WO | WO 98/12663 | 3/1998 |
| WO | WO 98/35720 A3 | 8/1998 |
| WO | WO 98/35720 A2 | 8/1998 |
| WO | WO 99/05971 | 2/1999 |
| WO | WO 00/07501 | 2/2000 |

OTHER PUBLICATIONS

Freeman, H.; "Computer Processing of Line Drawing Images"; Computing Surverys 6, 1974, pp. 57–97.

Besl, Paul J., *Member, IEEE*, and McKay, Neil D.; IEEE Transactions on Pattern Analysis and Machine Intelligence, vol. 14. No. 2, Feb. 1992; A Method for Registration of 3–D Shapes; pp. 239–256.

Fang, Shu–Cherng; Puthenpura, Sarat; AT&T; Linear Optimization and Extensions: Theory and Algorithms; Complexity Analysis and the Ellipsoid Method, Chap. 5, pp. 96–103.

(List continued on next page.)

Primary Examiner—Marvin M. Lateef
Assistant Examiner—Jeoyuh Lin
(74) Attorney, Agent, or Firm—Frederick L. Herman; Louis J. Capezzuto

(57) ABSTRACT

A condition, such as an electrical property, of a chamber of a heart is surveyed with a catheter having a condition sensor at its distal tip. A method for surveying the chamber includes the steps of acquiring a first image of the chamber containing topographical information, advancing the distal tip of the catheter into the chamber, acquiring a second image including a representation of the catheter distal tip in the chamber, displaying a superposition of the topographical information extracted from the first image with the second image to generate a displayed superimposed image, acquiring condition information at a point on the chamber displayed on the superimposed image on or near the topographical information, and acquiring condition information at one or more additional points sufficient in number and spacing to permit the generation of a survey map of the condition in the chamber. The method preferably further includes marking the display of the superimposed image to identify the points on the chamber at which the condition information was acquired.

47 Claims, 5 Drawing Sheets

U.S. PATENT DOCUMENTS

| | | | | |
|---|---|---|---|---|
| 4,522,212 | A | 6/1985 | Gelinas et al. | 128/642 |
| 4,628,937 | A | 12/1986 | Hess et al. | 128/642 |
| 4,630,203 | A | 12/1986 | Szirtes | |
| 4,660,571 | A | 4/1987 | Hess et al. | 128/784 |
| 4,682,603 | A | 7/1987 | Franz | 128/642 |
| 4,699,147 | A | 10/1987 | Chilson et al. | 128/642 |
| 4,875,165 | A | 10/1989 | Fencil et al. | |
| 4,878,115 | A | 10/1989 | Elion | 358/111 |
| 4,892,104 | A | 1/1990 | Ito et al. | |
| 4,898,181 | A | 2/1990 | Kessier | 128/699 |
| 4,905,705 | A | 3/1990 | Kizakevich et al. | 128/696 |
| 4,911,174 | A | 3/1990 | Pederson et al. | 128/695 |
| 4,922,912 | A | 5/1990 | Watanabe | 128/642 |
| 4,940,064 | A | 7/1990 | Desai | 128/784 |
| 4,955,382 | A | 9/1990 | Franz et al. | 128/642 |
| 4,962,767 | A | 10/1990 | Brownlee | 128/786 |
| 4,979,510 | A | 12/1990 | Franz et al. | 128/642 |
| 5,022,396 | A | 6/1991 | Watanabe | 128/642 |
| 5,038,791 | A | 8/1991 | Collins et al. | 128/696 |
| 5,042,486 | A | 8/1991 | Pfeiler et al. | 128/653 |
| 5,056,524 | A | 10/1991 | Oe | 128/654 |
| 5,127,403 | A | 7/1992 | Brownlee | 128/419 P |
| 5,146,926 | A | 9/1992 | Cohen | |
| 5,156,151 | A | 10/1992 | Imran | 128/642 |
| 5,175,773 | A | 12/1992 | Garreau et al. | |
| 5,215,103 | A | 6/1993 | Desai | 128/784 |
| 5,227,969 | A | 7/1993 | Waggener et al. | |
| 5,228,442 | A | 7/1993 | Imran | 128/642 |
| 5,231,995 | A | 8/1993 | Desai | 128/784 |
| 5,239,999 | A | 8/1993 | Imran | 128/642 |
| 5,243,981 | A | 9/1993 | Hudrlik | 607/11 |
| 5,255,678 | A | 10/1993 | Deslauriers et al. | 128/642 |
| 5,255,679 | A | 10/1993 | Imran | 128/642 |
| 5,279,299 | A | 1/1994 | Imran | 128/642 |
| 5,285,786 | A | 2/1994 | Fuji | |
| 5,289,373 | A | 2/1994 | Zarge et al. | |
| 5,293,869 | A | 3/1994 | Edwards et al. | 128/642 |
| 5,297,549 | A | 3/1994 | Beatty et al. | 128/642 |
| 5,311,866 | A | 5/1994 | Kagan et al. | |
| 5,311,873 | A | * 5/1994 | Savard et al. | 128/696 |
| 5,313,943 | A | 5/1994 | Houser et al. | 128/642 |
| 5,324,284 | A | 6/1994 | Imran | 606/15 |
| 5,341,807 | A | 8/1994 | Nardella | 128/642 |
| 5,345,936 | A | 9/1994 | Pomeranz et al. | 138/642 |
| 5,383,917 | A | 1/1995 | Desai et al. | 607/702 |
| 5,391,199 | A | 2/1995 | Ben-Haim | 607/122 |
| 5,409,000 | A | 4/1995 | Imran | 128/642 |
| 5,433,198 | A | 7/1995 | Desai | 128/642 |
| 5,443,489 | A | 8/1995 | Ben-Haim | 607/115 |
| 5,454,370 | A | 10/1995 | Avitall | 128/642 |
| 5,458,116 | A | 10/1995 | Egler | |
| 5,471,982 | A | 12/1995 | Edwards et al. | |
| 5,485,849 | A | 1/1996 | Panescu et al. | 128/699 |
| 5,487,391 | A | 1/1996 | Panescu | 128/699 |
| 5,515,853 | A | 5/1996 | Smith et al. | |
| 5,531,227 | A | 7/1996 | Scheider | |
| 5,546,951 | A | 8/1996 | Ben-Haim | 128/702 |
| 5,549,109 | A | 8/1996 | Samson et al. | 128/642 |
| 5,588,432 | A | 12/1996 | Crowley | 128/660.03 |
| 5,595,183 | A | 1/1997 | Swanson et al. | 128/697 |
| 5,637,090 | A | 6/1997 | McGee et al. | 604/95 |
| 5,640,967 | A | 6/1997 | Fine et al. | |
| 5,657,755 | A | 8/1997 | Desai | 128/642 |
| 5,687,737 | A | 11/1997 | Branham et al. | |
| 5,694,945 | A | * 12/1997 | Ben-Haim | |
| 5,697,377 | A | 12/1997 | Wittkampf | 128/696 |
| 5,718,241 | A | 2/1998 | Ben-Haim et al. | 128/702 |
| 5,730,704 | A | 3/1998 | Avitall | 600/374 |
| 5,734,739 | A | * 3/1998 | Sheehan et al. | 382/128 |
| 5,738,096 | A | 4/1998 | Ben-Haim | 128/653.1 |
| 5,755,664 | A | 5/1998 | Rubenstein | 600/377 |
| 5,782,773 | A | 7/1998 | Kuo et al. | |
| 5,797,396 | A | * 8/1998 | Geiser et al. | 384/128 |
| 5,803,084 | A | 9/1998 | Olson | |
| 5,820,568 | A | 10/1998 | Willis | |
| 5,830,150 | A | 11/1998 | Palmer et al. | |
| 5,840,031 | A | 11/1998 | Crowley | 600/440 |
| 5,842,984 | A | 12/1998 | Avitall | 600/374 |
| 5,871,019 | A | * 2/1999 | Belohlavek | 600/441 |
| 5,889,524 | A | 3/1999 | Sheehan et al. | 345/419 |
| 5,918,820 | A | 6/1999 | Bladen et al. | |
| 5,921,924 | A | 7/1999 | Avitalll | 600/374 |
| 5,931,835 | A | 8/1999 | Mackey | 606/34 |
| 5,931,863 | A | 8/1999 | Griffin, III et al. | 607/122 |
| 5,951,485 | A | 9/1999 | Cyrus et al. | |
| 5,999,587 | A | 12/1999 | Ning et al. | |
| 6,047,080 | A | 4/2000 | Chen et al. | |
| 6,052,618 | A | 4/2000 | Dahlke et al. | |
| 6,059,731 | A | * 5/2000 | Seward et al. | 600/459 |
| 6,066,094 | A | 5/2000 | Ben-Haim | |

OTHER PUBLICATIONS

Lai, Kok Fung; Thesis, University of Wisconsin–Madison 1994; Deformable Contours: Modeling, Extraction, Detection and Classification; 96 pgs.

Umeyama, Shinji; IEEE Transactions on Pattern Analysis and Machine Intelligence, vol. 13, No. 4, Apr. 1991; Least–Squares Estimation of Transformation Parameters Between Two Point Patterns; pp. 376–380.

Castleman, K.R.; Digital Image Processing (1996); "Curve and Surface Fitting"; pp. 501–507.

Jain, A.K.; Fundamentals of Digital Image Processing (1989); "The Back–Projection Operator"; pp. 445.

Foley J.D., van Dam A., Feiner S.K., Hughes J.F.; 2nd Edition in C Computer Graphics Principles and Practice (1996) ;"Filling Algorithms"; pp. 979–986.

Gerstenfeld E., Sahakian A., Swiryn S.; Evidence for Transient Linking of Atrial Excitation During Atrial Fibrillation in Humans (1992); Circulation vol. 86, No. 2, pp 375–382.

Gerstenfeld E., Sahakian A., Baerman J., Ropella K., Swiryn S.; Detection of Changes in Atrial Endocardial Activation With Use of an Orthogonal Catheter (1991); JACC vol. 18, No. 4, pp 1034–1042.

Kadish A., Spear J., Levine J., Hanich R., Prood C., Moore E.; Vector Mapping of Myocardial Activation (1986); Laboratory Investigation Arrhythmia vol. 74, No. 3, pp 603–615.

Kass et al.; Proceedings of First International Conference Vision (1987); Snakes: Active Contour Models; pp 259–268.

Terzopoulos D.; Transactions on Pattern Analysis and Machine Intelligence (1986), vol. PAMI–8, No. 4; Regularization of Inverse Visual Problems Involving Discontinuities; pp 413–424.

Lai et al.; IEEE Transactions on Pattern Analysis and Machine Intelligence (1995) vol. 17, No. 11; Deformable Contours: Modeling and Extraction; pp 1084–1090.

Onnasch et al.; Computers in Cardiology, Long Beach, CA, IEEE Computer Society (1975); A Versatile Program for the Documentation and Comparison of Traced Heart Contours; pp 257–262.

Duda et al.; Communications of the ACM (1972) vol. 15, No. 1; Use of the Hough Transformation to Detect Lines and Curves in Pictures; pp 11–15.

Copy of Partial European Search Report (Appln. No. EP 00 30 8248).

* cited by examiner

(12)  United States Patent US 6,385,476 B1

METHOD AND APPARATUS FOR INTRACARDIALLY SURVEYING A CONDITION OF A CHAMBER OF A HEART

FIELD OF THE INVENTION

The invention relates generally to methods and apparatus for surveying a condition of an organ of a subject, and particularly to methods and apparatus for surveying the electrical activity of one or more chambers of the heart.

BACKGROUND OF THE INVENTION

Cardiac arrhythmias, the most common of which is ventricular tachycardia (VT), are a leading cause of death. In a majority of patients, VT originates from a 1 mm to 2 mm lesion located close to the inner surface of the heart chamber. One of the treatments for VT comprises mapping the electrical pathways of the heart to locate the lesion followed by ablation of the active site.

U.S. Pat. No. 5,546,951 and U.S. patent application Ser. No. 08/793,371, which are incorporated herein in their entirety by reference, disclose methods for sensing an electrical property of the heart tissue, for example, local activation time, as a function of the precise location within the heart. The data are acquired with one or more catheters that are advanced into the heart, the catheters having electrical and location sensors in their distal tips. Methods of creating a map of the electrical activity of the heart based on these data are disclosed in commonly assigned U.S. patent application Ser. Nos. 09/122,137 and 09/357,559 filed on Jul. 24, 1998 and Jul. 22, 1999, respectively, which are also incorporated herein in their entirety by reference. As indicated in these applications, location and electrical activity is preferably initially measured on about 10 to about 20 points on the interior surface of the heart. These data points are then generally sufficient to generate a preliminary reconstruction or map of the cardiac surface to a satisfactory quality. The preliminary map may be combined with data taken at additional points in order to generate a more comprehensive map of the heart's electrical activity. The detailed map so obtained may then serve as the basis for deciding on a therapeutic course of action, for example, tissue ablation, to alter the propagation of the heart's electrical activity and to restore normal heart rhythm.

Catheters containing position sensors may be used to determine the trajectory of points on the cardiac surface. These trajectories may be used to infer the motion characteristics such as the contractility of the tissue. As disclosed in U.S. Pat. No. 5,738,096, incorporated herein in its entirety by reference, maps depicting such motion characteristics may be constructed when the trajectory information is sampled at a sufficient number of points in the heart. A high quality preliminary map of motion characteristics is dependent on acquiring a sufficient number of points representatively spaced about the heart chamber volume.

In constructing these preliminary maps, it is desirable that the data are sampled at points sufficiently spaced to outline the entire volume of the chamber under study. If the preliminary map adequately outlines the heart volume, acquisition of additional points will generally enable the detailed reconstruction to permit accurate diagnosis and treatment. Occasionally however, incomplete sampling, as, for example, by localizing the sample points to only a portion of the heart volume, will result in the generation of an incomplete map. Further sampling may lead to a more detailed map of the partial cardiac volume, but this may be inadequate for proper diagnosis and treatment.

In creating maps of the heart using the above-referenced systems, the initial data points for the preliminary reconstruction are generally acquired under the guidance of an imaging modality such as fluoroscopy that permits the cardiologist to observe the placement of the catheter tip within the heart chamber. Once the preliminary map is generated, subsequent points may then be acquired under the guidance of the preliminary map and a location system based on, for example, electromagnetic or acoustic sensors. Unfortunately, unassisted fluoroscopy provides relatively poor visualization of topographical features within the heart. While contrast-assisted fluoroscopy, in which a contrast agent is injected into the heart chamber under examination, significantly improves the observation of topography, the contrast agent obscures the observation of the catheter tip. Thus, fluoroscopy is insufficient to properly guide the cardiologist to the points on the interior of the heart necessary for the generation of a preliminary map of the electrical activity that roughly encompasses the complete heart volume. The potentially harmful effects of ionizing radiation to the patient also limit the amount of data that can be collected under fluoroscopy.

Electrical activity at a point in the heart is typically measured by advancing a catheter containing an electrical sensor at or near its distal tip to that point in the heart, firmly contacting the tissue with the sensor and acquiring data at that point. Alternatively, electrical activity may be measured with catheters containing multiple electrodes.

It is generally important to maintain good electrical contact between the electrodes and the tissue in order to obtain a reliable and stable electrical reading. Fluoroscopy produces images that are lacking in topographical detail. Accordingly, in taking measurements under the guidance of this imaging modality, the catheter tip may not actually be in effective contact with the tissue. Alternatively, it may be possible to bruise the intracardial tissue by excessive pressure of the catheter tip against the tissue while making such measurements.

SUMMARY OF THE INVENTION

The present invention is directed to a method for intracardially surveying a condition of a chamber of a heart of a subject. The method of the invention is accomplished by use of a catheter having a distal tip with a condition sensor contained therein or proximate thereto. The condition sensor is capable of sensing condition information of the heart chamber. The method of the invention comprises the steps of:

a) acquiring a first image of the chamber which contains topographical information of the chamber;
b) advancing the catheter distal tip into the chamber;
c) acquiring a second image comprising a representation of the catheter distal tip in the chamber;
d) displaying a superposition of topographical information acquired in step (a) with the second image of step (c) to generate a displayed superimposed image comprising representations of the topographical information and the catheter distal tip;
e) acquiring condition information at an acquisition point on the chamber with the condition sensor, the acquisition point being selected from points on the displayed superimposed image of step (d) proximate the topographical information;
f) repeating step (e) at one or more additional acquisition points, the points being sufficient in number and spacing throughout the chamber to permit the generation of a survey map of the condition in the chamber.

In a preferred embodiment, the method of the invention comprises the steps of:
a) acquiring a first, contrast-assisted fluoroscopic image of the chamber;
b) creating a contour image of the interior of the chamber from the contrast-assisted fluoroscopic image;
c) advancing the distal tip of the catheter into the chamber;
d) acquiring a second, non-contrast-assisted fluoroscopic image comprising a representation of the catheter distal tip in the chamber. The first image and the second image are acquired from a common projection relative to the subject;
e) displaying a superposition of the contour image of step (b) with the fluoroscopic image of step (d) to generate a superimposed image;
f) acquiring condition information at an acquisition point on the chamber with the condition sensor, the acquisition point being selected from points on the displayed superimposed image of step (e) proximate the topographical information;
g) repeating step (f) one or more times at one or more additional acquisition points, the points being sufficient in number and spacing throughout the chamber to permit the generation of a survey map of the condition in the chamber.

In another preferred embodiment, the method of the invention comprises the steps of:
a) acquiring a first, contrast-assisted fluoroscopic image of the chamber, the first, contrast-assisted fluoroscopic image being acquired from a first projection relative to the subject;
b) creating a first contour image of the interior of the chamber from the first contrast-assisted fluoroscopic image;
c) acquiring a second, contrast-assisted fluoroscopic image of the chamber, the second, contrast-assisted fluoroscopic image being acquired from a second projection relative to the subject;
d) creating a second contour image of the interior of the chamber from the second contrast-assisted fluoroscopic image;
e) advancing the distal tip of the catheter into the chamber;
f) acquiring a first non-contrast-assisted fluoroscopic image comprising a representation of the catheter distal tip in the chamber, the first non-contrast-assisted fluoroscopic image being acquired from the first projection relative to the subject;
g) displaying a superposition of the first contour image of step (b) with the first non-contrast-assisted fluoroscopic image of step (f) to generate a first superimposed image;
h) acquiring the condition information at an acquisition point on the chamber with the condition sensor, the acquisition point being selected from points on the displayed superimposed image of step (g) proximate the first contour image;
i) acquiring a second non-contrast-assisted fluoroscopic image comprising a representation of the catheter distal tip in the chamber, the second non-contrast-assisted fluoroscopic image being acquired from the second projection relative to the subject;
j) displaying a superposition of the second contour image of step (d) with the second non-contrast-assisted fluoroscopic image of step (i) to generate a second superimposed image;
k) acquiring the condition information at an acquisition point on the chamber with the condition sensor, the acquisition point being selected from points on the displayed superimposed image of step (j) proximate the second contour image;
l) repeating steps (h) and (k) at one or more additional acquisition points, the points being sufficient in number and spacing throughout the chamber to permit the generation of a survey map of the condition in the chamber.

In another preferred embodiment, the method of the invention further comprises the step of marking the display of the superimposed image to identify the points on the chamber on which the condition information was acquired.

The invention is also directed to apparatus for intracardially surveying a condition of a chamber of a heart of a subject. The apparatus of the invention comprises:
a) means for displaying a superposition of topographical information from a first acquired image with a second image; and
b) means for acquiring condition information at a number of points in the chamber, the points being sufficient in number and spacing throughout the chamber to permit the generation of a survey map of the condition in the chamber.

In a preferred embodiment, the apparatus of the invention further comprises means for marking the display to identify the points in the chamber at which the condition information was acquired.

In another preferred embodiment, the apparatus of the invention further comprises means for generating the topographical information from the first image.

It is an object of the invention to provide a method for surveying a condition of a chamber of the heart to permit the generation of a preliminary map of the condition in the chamber.

It is another object of the invention to provide a method for surveying a chamber of the heart that avoids collection of data localized in only a portion of the sampling volume.

It is another object of the invention to provide a method for surveying the condition of a chamber of the heart to permit the reconstruction of detailed maps that enable more accurate diagnosis and treatment of the heart.

It is another object of the invention to provide a method for surveying a chamber of the heart that reduces the likelihood of injury to heart tissue during sampling of the condition data.

It is another object of the invention to provide a method for surveying a condition of a chamber of the heart that minimizes the adverse effects of ionizing radiation during collection of the survey data.

It is another object of the invention to provide a method for surveying a condition of a chamber of the heart that provides the capability to mark the displayed information to indicate the points on the heart at which such information was acquired.

It is another object of the invention to provide an apparatus to survey the condition of a chamber of the heart in a process that possesses the above-enumerated attributes.

These and other objects, features and advantages will be more readily apparent from the detailed description set forth below, taken in conjunction with the accompanying drawings.

DETAILED DESCRIPTION OF PREFERRED EMBODIMENTS

Figure 1:
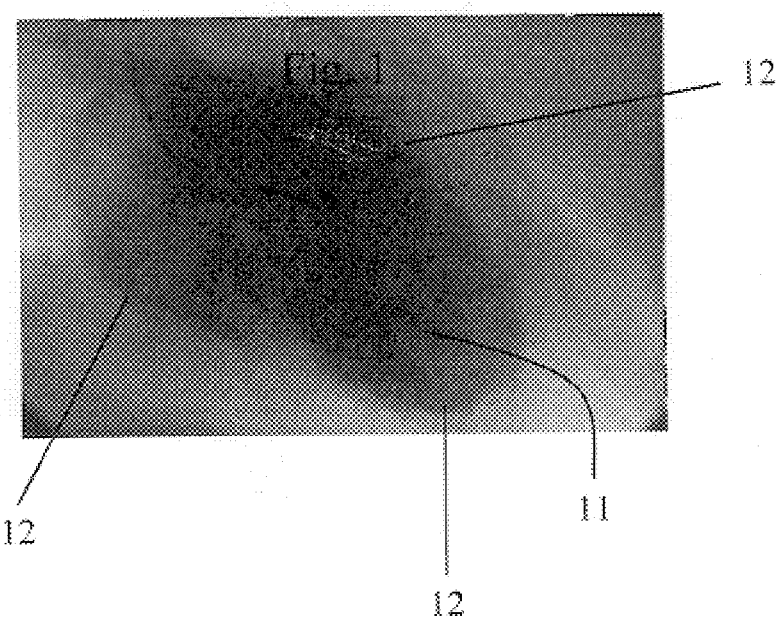
FIG. 1 is an LV-gram image of the left ventricle of a human heart taken from the right anterior oblique (RAO) projection.

The present invention is directed to methods and apparatus for intracardially surveying a condition of a chamber of a heart of a subject. The method and apparatus of the invention are amenable to surveying the condition of any of the heart's chambers, but they are particularly useful in surveying the condition of the left ventricle of the heart.

The method and apparatus of the invention may be used to survey one or more conditions or properties of the tissue comprising the chambers of the heart. As used herein, the term "condition" refers to either a scalar or a vector quantity, and may comprise, for example, an electrical property, a temperature, a pressure, a pH, a measure of local heart movement or any other condition or combination thereof. The method and apparatus of the invention are especially useful for surveying electrical properties of a heart chamber, including but not limited to voltage, impedance, conduction velocity and local activation time (LAT).

As used herein, the term "survey" refers to the collection of data as to the condition of the chamber at representative points throughout the chamber. The condition information may be collected individually, or it may be collected together with position information so that each data point would reflect the condition information at a given three dimensional coordinate within the chamber. If many points are sampled during the survey, the survey may be useful in providing a comprehensive representation of the condition information throughout the heart chamber. Alternatively, the survey may be preliminary, in which relatively few points are sampled around the chamber. However, even in the case of a preliminary survey, if the points are sufficient in number and in distribution around the chamber, the resultant data may be used for establishing a "boundary map" of the chamber, the detailed state of which may be determined using subsequent more comprehensive sampling. The method and apparatus of the invention are especially useful for conducting such preliminary surveys.

The invention will now be described in terms of a method and apparatus for measuring the electrical properties of the heart. However, it will be understood that using the appropriate sensors, the method is equally applicable to measuring any of the above-enumerated conditions.

The condition of the heart chamber is measured by one or more sensors contained at or proximate the distal tip of a catheter which is advanced into the chamber being surveyed. In the case of a catheter having a single condition sensor, the sensor is preferably contained at the catheter distal tip. Using such a single condition sensor catheter in the method of the invention, the condition information of the tissue in the chamber is sensed and acquired on a point-by-basis. The condition at any point in the chamber is determined by advancing the catheter to that point, preferably contacting the tissue at that point with the sensor contained at the catheter distal tip, and acquiring the condition information over some time period. Typically, the data at each point are acquired as a function of time for one or more cardiac cycles. The data are then stored in computer memory for future use, as, for example, in the construction of a two or three dimensional map which graphically depicts the measured condition over all or a portion of the chamber.

Catheters used in the method and apparatus of the invention may have more than one condition sensor contained therein. Catheters containing multiple sensors that may be useful in characterizing the electrical properties the heart tissue are described, for example in U.S. Pat. Nos. 5,409,000; 5,588,432; 5,931,863; 5,931,835; and 5,921,924, which are hereby incorporated in their entirety by reference. The use of multi-sensor catheters in the method and apparatus of the invention permit the simultaneous measurement of condition information at multiple points in the heart chamber, which can potentially decrease the time required for assessing the overall condition of the heart chamber.

The catheter used in the method and apparatus of the invention preferably further comprises one or more sensors proximate its distal tip that may be used to accurately measure the position and or the orientation of the catheter tip in the body, particularly, in the heart of the subject. The position sensor may, for example, operate by sensing or transmitting acoustic, magnetic or electromagnetic fields. An electromagnetic field sensor is preferred as a position sensor. Preferably, position information is sensed by the position sensors and acquired simultaneous with the sensing of condition information by the condition sensor. Catheters having sensors capable of use in measuring both electrical properties of the heart tissue as well as the location of the catheter tip are described for example in U.S. patent application Ser. No. 08/793,371 and in PCT application WO96/05768, which are hereby incorporated in their entirety by reference. By way of example, the NAVI-STAR™ catheter, available from Biosense-Webster, Inc. of Diamond Bar, Calif., is a catheter having both electrical condition and position sensors contained therein that may be useful in practicing the method of the present invention.

The catheter used in the method and apparatus of the invention may further comprise means for effecting therapies to the tissue comprising the heart chamber. For example, endocardial ablation is well known in the art as a therapeutic technique for correcting cardiac arrhythmia. Such therapy may, for example, be effected by delivering radiofrequency energy to the diseased tissue from an electrode contained on the catheter distal tip.

The method of the invention broadly comprises the following steps:

a) acquiring a first image of the chamber which contains topographical information of the chamber;
b) advancing the distal tip of the catheter into the chamber;
c) acquiring a second image comprising a representation of the catheter distal tip in the chamber;
d) displaying a superposition of topographical information acquired in step (a) with the second image of step (c) to generate a displayed superimposed image comprising representations of the topographical information and the catheter distal tip;
e) acquiring condition information at an acquisition point on the chamber with the condition sensor, the acquisition point being selected from points on the displayed superimposed image of step (d) proximate the topographical information;, f) repeating step (e) at one or more additional acquisition points, the points being sufficient in number and spacing throughout the chamber to permit the generation of a survey map of the condition in the chamber.

The first step in the method of the invention is to acquire a first image of the heart chamber that contains topographical information. The topographical features typically depicted in the image include the boundary or contour of the interior of the chamber, although other topographical or pathological features may also be depicted. Exemplary imaging modalities that may be used to acquire the first image include single photon emission computerized tomography (SPECT), positron emission tomography (PET), two or three dimensional echo cardiography, magnetic resonance imaging (MRI), computerized tomography (CT) and fluoroscopy. Some of these modalities, e.g., fluoroscopy, may require the injection of a contrast agent into the blood stream or into the chamber to visualize the topographical features of the chamber. Due to the fact that fluoroscopy is a commonly found imaging modality in catheterization laboratories, contrast-assisted fluoroscopy is the preferred imaging modality for acquiring the first image containing topographical information in the method of the invention.

In the case of contrast-assisted fluoroscopy, and perhaps with other imaging modalities, the first image of the chamber containing topographical information is acquired dynamically, i.e., sequential images are acquired after injection of the contrast agent. Sequential images are acquired for at least one and preferably several cardiac cycles. In effect, a multiple frame "moving picture" of the chamber is acquired. In some applications of the method of the invention, it is preferable to select a single frame of the dynamically acquired image for subsequent use in the method of the invention. For these applications, the single frame corresponding to the end-diastole portion of the cardiac cycle is preferred. On the other hand, any other frame may be selected, provided that it is used consistently for extraction of the contour as well as subsequent display of images containing representations of the catheter tip.

The end diastole point in the cardiac cycle is the point at which the ventricles are maximally dilated immediately prior to contraction. The frame corresponding to or depicting the chamber in end diastole may be selected by a variety of methods. The frames may be viewed manually and the end diastole frame may be selected as the frame just prior to the ventricular contraction. Alternatively, the end diastole frame may be determined automatically using image processing techniques. For example, the boundary or contour of the chamber in each frame may be extracted using an algorithm such as snakes. The frame whose contour bounds the maximum area corresponds to the end diastole frame. Alternatively, the frame corresponding to end diastole may be correlated with the body surface electrocardiogram (ECG). Specifically, the end diastole frame may be defined by a particular feature of the QRS wave of the body surface ECG.

In the case in which the left ventricle (LV) is the object of the study, the first image preferably comprises a contrast-assisted fluoroscopy image of the left ventricle, commonly referred to as an LV-gram. An LV-gram image of the a human heart showing the ventricle in end diastole, taken from the right anterior oblique (RAO) projection, is shown in FIG. 1. As seen in FIG. 1, the dark area 11 depicts the interior of the left ventricle filled with contrast agent. As the ventricle is completely filled with contrast agent, the topographical features of the ventricle, i.e., the ventricle border or contour 12, is clearly visible in the LV-gram.

Figure 2:
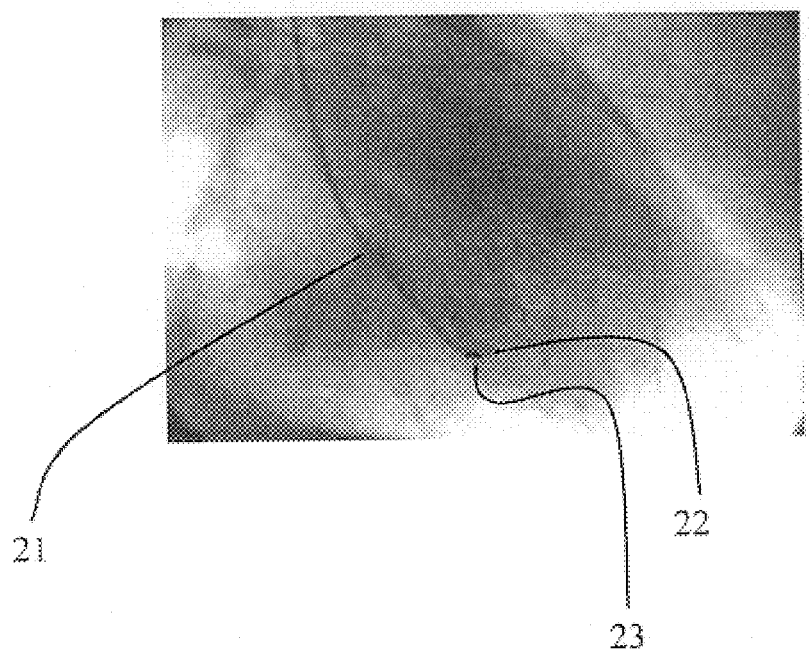
FIG. 2 is a fluoroscopic image of a catheter located in the heart of FIG. 1 taken from the RAO projection.

After the catheter comprising the condition sensor is advanced into the heart chamber being surveyed, the next step in the method of the invention involves acquiring a second image of the chamber showing the catheter contained therein. The second image may be acquired using one of a variety of imaging modalities, for example, fluoroscopy, echo cardiography, MRI or CT. Once again, due to the ubiquitous nature of fluoroscopy in the catheterization laboratory, fluoroscopy is the preferred modality for obtaining the second image in the method of the invention. FIG. 2 shows a fluoroscopic image of the heart of FIG. 1 taken from an RAO projection. The image in FIG. 2 shows the catheter 21 having distal tip 22 with an electrical sensor 23 contained therein. As shown in FIG. 2, however, the non-contrast-assisted fluoroscopic image is not particularly helpful in providing readily discernible visual guidance as to the internal ventricle walls. Furthermore, the fluoroscopic image extends to the epicardium. Accordingly, sampling the condition information at the endocardium under fluoroscopic guidance alone may lead to incomplete sampling in only a portion of the heart chamber and may be less informative in terms of identifying sampling points on the endocardial wall.

The next step in practicing the method of the invention involves displaying a superposition of the topographical information from the first image with the second image comprising a representation of the catheter distal tip 22. In the practice of the method of the invention using dynamically acquired imaging modalities, a variety of superpositions may be performed in displaying the topographical information together with the image showing the catheter tip 22. In the case of contrast-assisted fluoroscopy as the modality for acquiring the first image containing topographical information of the chamber, the contrast-assisted image is dynamically acquired. Accordingly, either a dynamic moving image of the chamber or a static image at a single point in the cardiac cycle may be used in the displayed superposition. Likewise, non-contrast assisted fluoroscopy used to image the catheter tip 22 in the chamber is also dynamically acquired, so that either a dynamic or static image showing the catheter tip may be used.

The purpose of creating the superposed displayed image is two-fold. First, to facilitate the guidance of the catheter tip 22 to the wall of the chamber under examination, and second, to provide a visualization that will permit the cardiologist to acquire data at representative points throughout the chamber. Mere superposition of the images of FIG. 1 and FIG. 2 would be inadequate to serve these purposes, since the dark area of the LV-gram of FIG. 1 showing the interior of the left ventricle would completely obscure the image of the catheter tip 22. Accordingly, it is desirable to extract or derive the contour information from FIG. 1 prior to superposition with the image of FIG. 2.

Figure 3:
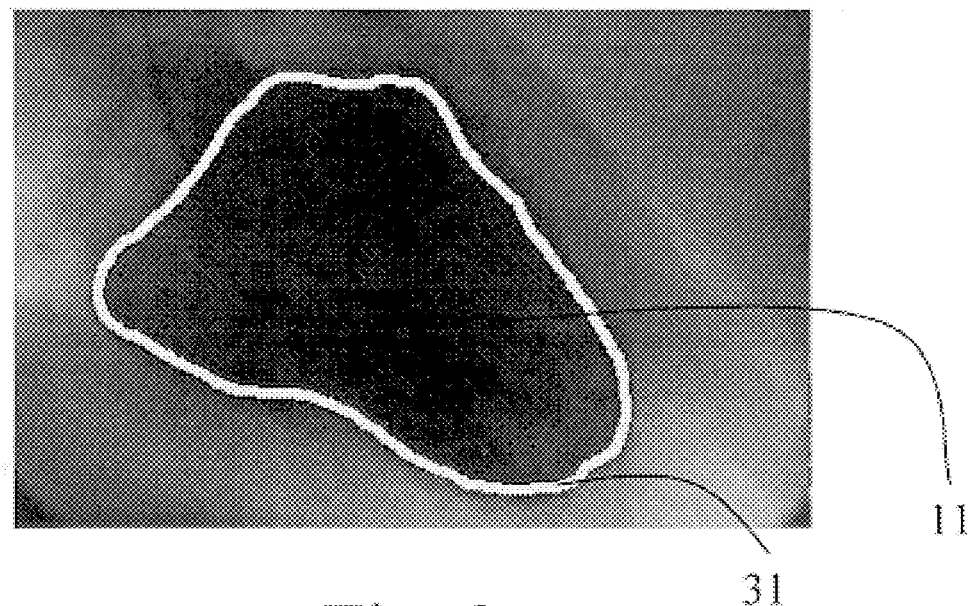
FIG. 3 is the LV-gram of FIG. 1 in which a contour image has been created about the interior of the left ventricle.

FIG. 3 is an LV-gram image of the ventricle shown in FIG. 1 in which contour image 31 has been created about the contour of the interior wall of ventricle 11. The contour image may be created, for example, in one of three ways:

A. Manual Creation of Contour Image—The contrast-assisted image is imported into a drawing program and a continuous contour image is manually traced around the entire ventricle contour using the drawing program drawing tool by manually dragging the mouse pointer or a similar pointing device completely around the contour. Alternatively, the contrast-assisted image may be manually marked at discrete points with the drawing tool and the contour may be interpolated between these points, using splines, for example.

B. Automatic Creation of Contour Image—The contour image is created and extracted automatically using a contour extraction algorithm such as snakes. Snakes were originally proposed as a regularization approach for locating contours (see M. Kass, A. Witkin & D. Terzopoulos, "Snakes: Active Contour Models," *Proceedings of First International Conference Vision*, 1998, pp. 259–269 and D. Terzopoulos, "Regularization of Inverse Visual Problems Involving Discontinuities," *IEEE Trans. Pat. Anal. Mach. Intell.*, vol. PAMI-8, no. 4, 1998, pp. 413–424).

The contour V may be represented as an ordered set of points, $V=[v_1, v_2, \ldots, v_n]$ wherein each $v_i$ is defined by a pair of (x, y) coordinates. A snake can be either closed or open, depending on whether the end points are connected. In the present invention, we preferably use closed snakes.

We denote two functionals $E_{int}$ and $E_{ext}$. $E_{int}(v_i)$ imposes continuity and smoothness constraints, wherein $E_{ext}(v_i)$ attracts the snake to salient image features, for example, the magnitude of the intensity gradient. We seek to minimize both $E_{int}$ and $E_{ext}$. Minimizing both functionals via the snake then turns the boundary extraction problem into the following energy minimization problem:

$$V_\Lambda = \arg\min_V \sum \lambda_i E_{int}(v_i) + (1-\lambda_i)E_{ext}(v_i) \quad (1)$$

wherein $\lambda_i \in [0,1]$ is a tradeoff parameter. Setting $\lambda$ to 0 means that we minimize only the $E_{ext}$ component of the equation. Setting $\lambda$ to 1 means minimizing only the $E_{int}$ component. Intermediate $\lambda$s result in a tradeoff of $E_{int}$ vs. $E_{ext}$.

The $\lambda$ parameter may be found empirically or by a parametric selection strategy based on the minimax criterion (see H. Freeman, "Computer processing of Line Drawing images," *Computer Survey* 6, 1974, pp. 57–98).

In the original formulation, the internal energy $E_{int}$ was defined by the first and the second derivatives along the boundary, giving the snake rubber-sheet and thin-plate like behavior respectively, and is approximated by $$E_{int}(v_i)=\|v_i-v_{i-1}\|^2+\|v_{i-1}-2v_i+v_{i+1}\|^2$$

Alternatively, $E_{int}(v_i)$ and $E_{ext}(v_i)$ may be defined in different ways, for example, as described by K. F. Lai & R. T. Chin, in "Deformable Contours: Modeling and Extraction", PAMI-17, No. 11, November 1995, pp. 1084–1090.

C. Semiautomatic Creation of Contour Image—In one variation of the semi-automatic method, the physician is presented with a snakes contour for acceptance or rejection. Rejection of the contour results in further processing leading to the presentation of another possible contour. This continues until the physician accepts the contour image. Alternatively, a modified snakes algorithm may be employed which forces the contour image to one or more points pre-selected by the user.

Figure 4:
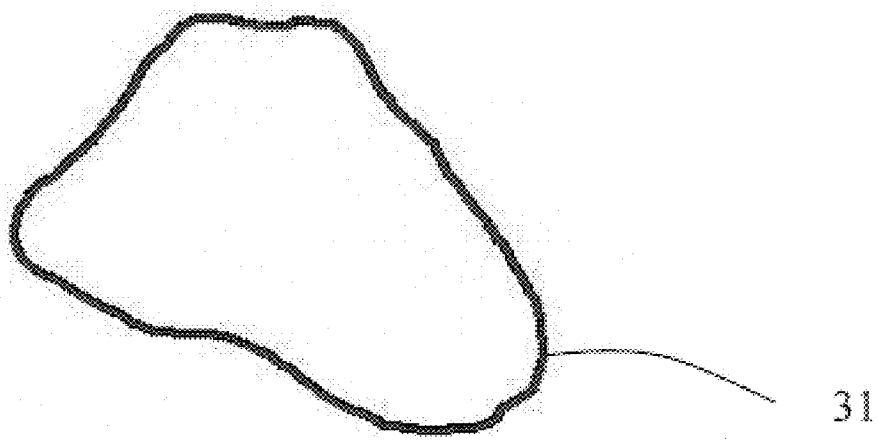
FIG. 4 is the extracted contour image of FIG. 3.

The contour image 31 so produced, extracted from the LV-gram, is shown in FIG. 4. The x, y coordinates of the extracted contour image are preferably stored in computer memory for use in displaying the superposition of topographical information and the image showing the catheter tip 22.

As indicated previously, the contour information and the image showing the catheter tip 22 may be either dynamic or static. The contour 31 and catheter tip 22 information may be superimposed, for example, in the following ways:

A. Static Contour Image on Static Catheter Tip Image

A static contour image is acquired from a dynamic image by one of the hereinabove described methods, e.g., the end diastole frame is acquired by synchronization with the body surface ECG signal. The fluoroscopy image showing the catheter tip 22 is also gated to show the same frame as that selected for the contour image. The superposition of the contour image on the image showing the catheter tip 22 is effected by changing the color or intensity of the pixels corresponding to the stored contour image in the image showing the catheter tip 22.

B. Static Contour Image on Dynamic Catheter Tip Image

The static contour image as hereinabove described is superimposed on a dynamic image of the catheter tip 22 in the heart. In this case, the pixel color or intensity of each frame of the dynamic fluoroscopy image is processed as described above to show the contour image 31 of the chamber 11.

C. Dynamic Contour Image on Dynamic Catheter Tip Image

Rather than selecting a single frame of the contrast-assisted image, the entire sequence is processed to extract the contour of each frame. The stored contours are then synchronized with the live dynamic images of the chamber 11 and catheter tip 22 and each frame of the live images is processed to adjust pixel color or intensity corresponding to the contour at that point in the cardiac cycle.

Figure 5:
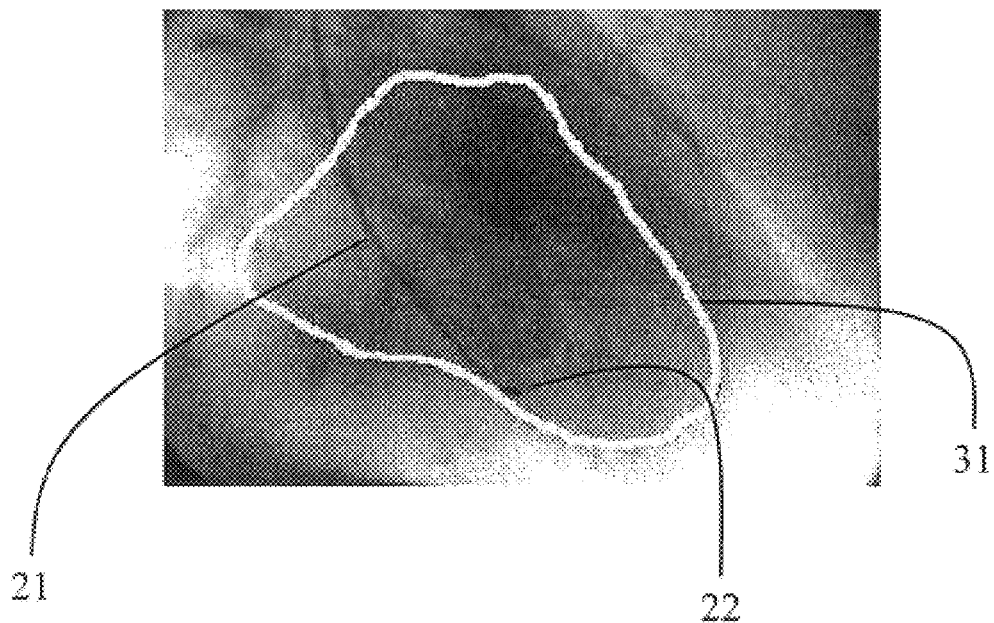
FIG. 5 is a superposition of the contour image of FIG. 4 and the fluoroscopic image of FIG. 2.

The resultant processed images showing the contour and the catheter tip 22 are shown on the display. FIG. 5 is a photograph of the displayed superposition of contour image 31 of FIG. 4 with the fluoroscopic image showing a portion of catheter 21 and catheter tip 22 of FIG. 2.

Since the first image containing the topographical information (FIG. 1) and the second image showing the catheter tip 22 (FIG. 2) were both acquired using the same imaging modality (fluoroscopy) and from the same projection (RAO), contour image 31 in the displayed superimposed image represents points on the interior wall of the chamber 11. Accordingly, in order to acquire condition information concerning the tissue of the chamber, the cardiologist advances the catheter tip 22 under the guidance of the displayed superimposed image of FIG. 5 to an acquisition point shown on the displayed image as being on or proximate to boundary image 31. At this acquisition point, the catheter tip 22 is in contact with or proximate to the chamber wall, and condition information, preferably together with location information, may be acquired. While viewing the displayed superimposed image, the cardiologist may acquire the condition and/or position information by activation of a foot pedal, for example, which instructs the computer to initiate data acquisition. Condition and/or position information are preferably acquired repetitively at each point on the wall of the cardiac chamber for at least one and preferably more than one complete cardiac cycle. Data are preferably acquired at a frequency of at least about 10 per second, more preferably, at a frequency of at least about 20 per second, and most preferably, at a frequency of at least about 50 per second.

After acquiring data at the first acquisition point, the cardiologist acquires subsequent data by advancing the catheter tip 22 to successive points in the chamber, such points being shown in the displayed superimposed image as being on or proximate to the contour image. The total number of data points acquired is a function of the intended purpose of the survey. If only a preliminary survey is being conducted in order to define the boundary of the chamber for another guidance or navigation technique, at least 3 and preferably at least 5 points should be acquired under the guidance of the displayed superimposed image.

As described herein, the first image containing topographical information and the second image containing a representation of the catheter tip 22 are preferably acquired using the same imaging modality, i.e., fluoroscopy. Furthermore, both images are preferably acquired in the same projection, i.e., the images of FIG. 1 and FIG. 2 were both acquired in the RAO projection. Acquiring both images using the same modality and using the same projection is preferred because this eliminates the need to register the images. Alternatively, the first and second images may be acquired using different imaging modalities and/or from different projections. However, such images would require registration during superposition if the displayed superposed image is to serve as a guide for the chamber contour.

To assist the cardiologist in acquiring representative condition information throughout the entire chamber, the method of the invention preferably comprises marking the display at the points at which condition information is acquired. This capability provides the cardiologist with a visual indication of all of the points or sites on the cardiac wall at which information was acquired, and helps guide the cardiologist to sites where sampling is still required.

The display is preferably marked automatically when means such as the foot pedal is activated to initiate data acquisition. The position of the catheter tip 22 in the display is preferably located automatically by the following algorithm. The catheter tip location algorithm is based on the following assumptions:

1) The catheter tip 22 is visualized as dark on the image;
2) The greatest contrast in the displayed superimposed image occurs between the catheter tip 22 and its surroundings; and
3) The size of the catheter tip 22 may be fixed in the analysis of all images.

Figure 8:
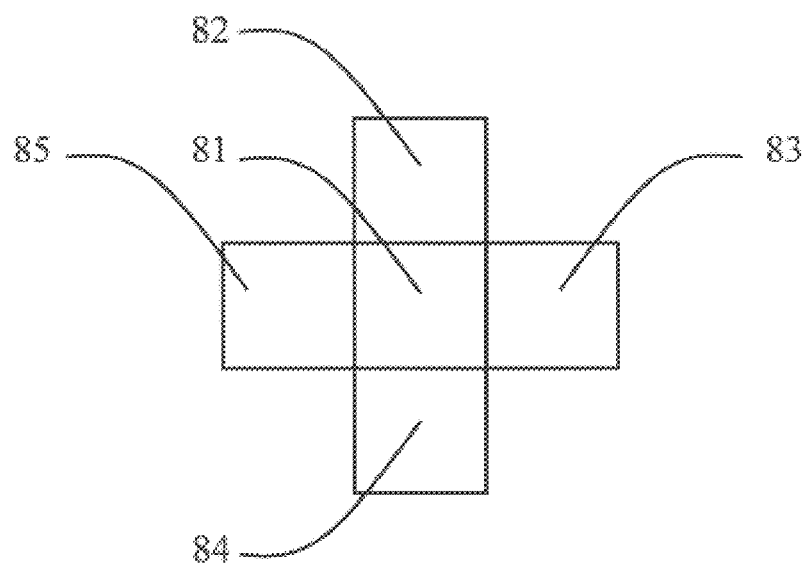
FIG. 8 is a representation of an algorithm used to automatically find a catheter tip in a displayed image.

The algorithm may be understood by reference to FIG. 8, in which the catheter tip 22 is approximated by a fixed geometric shape of a given size, for example square 81 in FIG. 8. Each square is of the same size, between about 10 to about 20 pixels. To test whether the catheter tip is visualized in square 81, the average intensity of the pixels comprising square 81 is computed. Similarly, the average intensity is evaluated for the pixels comprising the four squares, 82, 83, 84 and 85 surrounding square 81. The contrast between square 81 and its neighbors 82, 83, 84 and 85 is the difference in average intensity between square 81 and the average intensity of squares 82, 83, 84 and 85. This calculation is iterated about all pixels in the image. The catheter tip location is attributed to the square having the maximum contrast or intensity difference with its surroundings.

Marking the display helps the cardiologist to avoid missing regions of the heart if the objective is to survey the chamber as a whole. Marking the display to indicate the data acquisition sites also permits the cardiologist to return to a visited site, for example, to confirm previously sampled condition information.

The displayed superimposed image may be marked with a geometric symbol for example (e.g., a square, circle, etc.) to depict each point at which condition information was acquired. Alternatively, the display may be marked with a number or color representative of the magnitude of the condition information acquired at that point. The display may be marked, for example, by instructing the computer to mark the display with the position of the catheter tip when the foot pedal which initiates data acquisition is activated. Alternatively, the cardiologist may be provided with marking means which allows the selection of which of the acquired points are to be marked on the displayed superimposed image.

Figure 6:
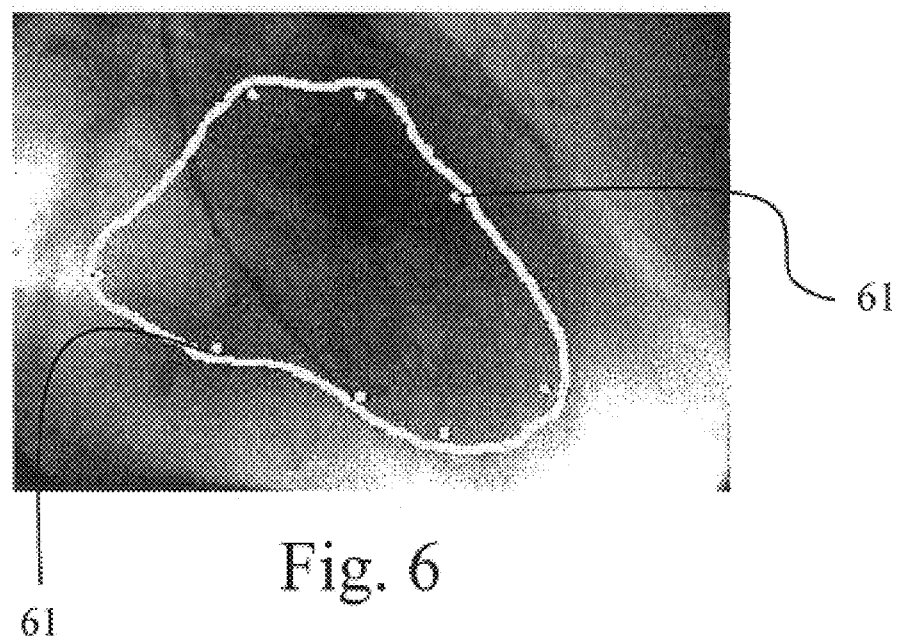
FIG. 6 is the image of FIG. 5 in which the display was marked to indicate points in the chamber from which condition information was acquired.

FIG. 6 depicts the displayed superimposed image of FIG. 5 in which geometric symbols 61 have been marked on the displayed image corresponding to the points in the chamber at which condition information was acquired.

The topographic information used in the method of the invention as heretofore described is two dimensional in nature. Accordingly, the contour image used in the displayed superimposed image only represents points on the interior wall of the heart chamber in a single plane. If the objective of the survey is a more comprehensive characterization of the heart chamber, it may be preferable to perform the method of the invention using images acquired from a plurality of projections. Briefly, the method of the invention in which image and condition information are acquired from two projections using fluoroscopy, the preferred imaging modality, comprises the steps of:

a) acquiring a first, contrast-assisted fluoroscopic image of the chamber, the first, contrast-assisted fluoroscopic image being acquired from a first projection relative to the subject;

b) creating a first contour image of the interior of the chamber from the first contrast-assisted fluoroscopic image;

c) acquiring a second, contrast-assisted fluoroscopic image of the chamber, the second, contrast-assisted fluoroscopic image being acquired from a second projection relative to the subject;

d) creating a second contour image of the interior of the chamber from the second contrast-assisted fluoroscopic image;

e) advancing the distal tip of the catheter into the chamber;

f) acquiring a first non-contrast-assisted fluoroscopic image comprising a representation of the catheter distal tip in the chamber, the first non-contrast-assisted fluoroscopic image being acquired from the first projection relative to the subject;

g) displaying a superposition of the first contour image of step (b) with the first non-contrast-assisted fluoroscopic image of step (f) to generate a first superimposed image;

h) acquiring the condition information at an acquisition point on the chamber with the condition sensor, the acquisition point being selected from points on the first superimposed image of step (g) proximate the first contour image;

i) acquiring a second non-contrast-assisted fluoroscopic image comprising a representation of the catheter distal tip in the chamber, the second non-contrast-assisted fluoroscopic image being acquired from the second projection relative to the subject;

j) displaying a superposition of the second contour image of step (d) with the second non-contrast-assisted fluoroscopic image of step (i) to generate a second superimposed image;

k) acquiring the condition information at an acquisition point on the chamber with the condition sensor, the acquisition point being selected from points on the second superimposed image of step proximate the second contour image;

l) repeating steps (h) and (k) at one or more additional acquisition points, the points being sufficient in number and spacing throughout the chamber to permit the generation of a survey map of the condition in the chamber.

Preferably, all of the data acquired under the guidance of one of the displayed superimposed images is collected before collecting data under the guidance of the second displayed superimposed image.

If only a preliminary survey is being conducted in order to define the boundary of the chamber for another guidance or navigation technique, at least 3 and preferably at least 5 points should be acquired under the guidance of each of the displayed superimposed images.

Figure 7:
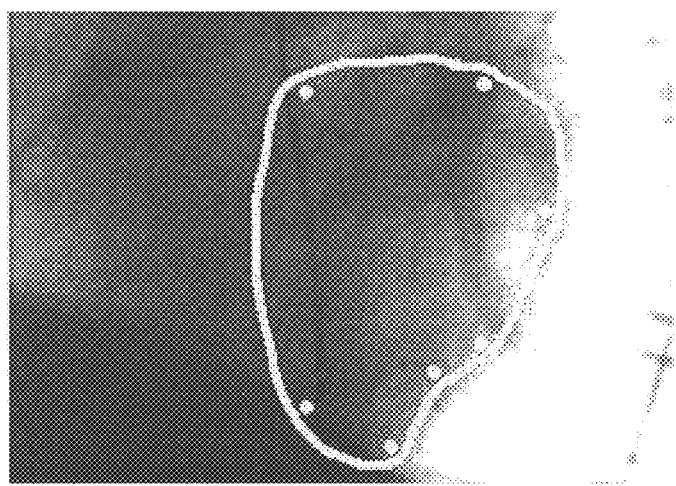
FIG. 7 is equivalent to the image of FIG. 6 taken from the left anterior oblique (LAO) projection.

As hereinabove described, the method of the invention preferably further comprises marking the points 61 on the superimposed image at which condition information was acquired. FIG. 7 shows a marked superposition of the contour and fluoroscopy images of the left ventricle shown in FIGS. 1–6 in which the images were acquired in a left anterior oblique (LAO) projection. Sampling the condition of the chamber from multiple projections is expected to increase the accuracy of a preliminary map of the heart chamber based on the data.

If the method of the invention is practiced with a catheter containing a sensor for obtaining position information, each data point of condition information obtained via the condition sensor may be accompanied by a three dimensional coordinate of the tissue at which the data point was obtained. The resulting survey data of condition and position information obtained by the practice of the method of the invention is especially useful for the creation of maps, especially 3-dimensional maps of the heart. Methods of creating such maps are disclosed in copending commonly assigned U.S. patent application Ser. Nos. 09/122,137 and 09/357,559 filed on Jul. 24, 1998 and Jul. 22, 1999, respectively, which are incorporated herein in their entirety by reference. The method of the invention further optionally comprises the step of creating a map of the condition of the heart based on the position and condition information obtained from the practice of the method of the invention.

Figure 9:
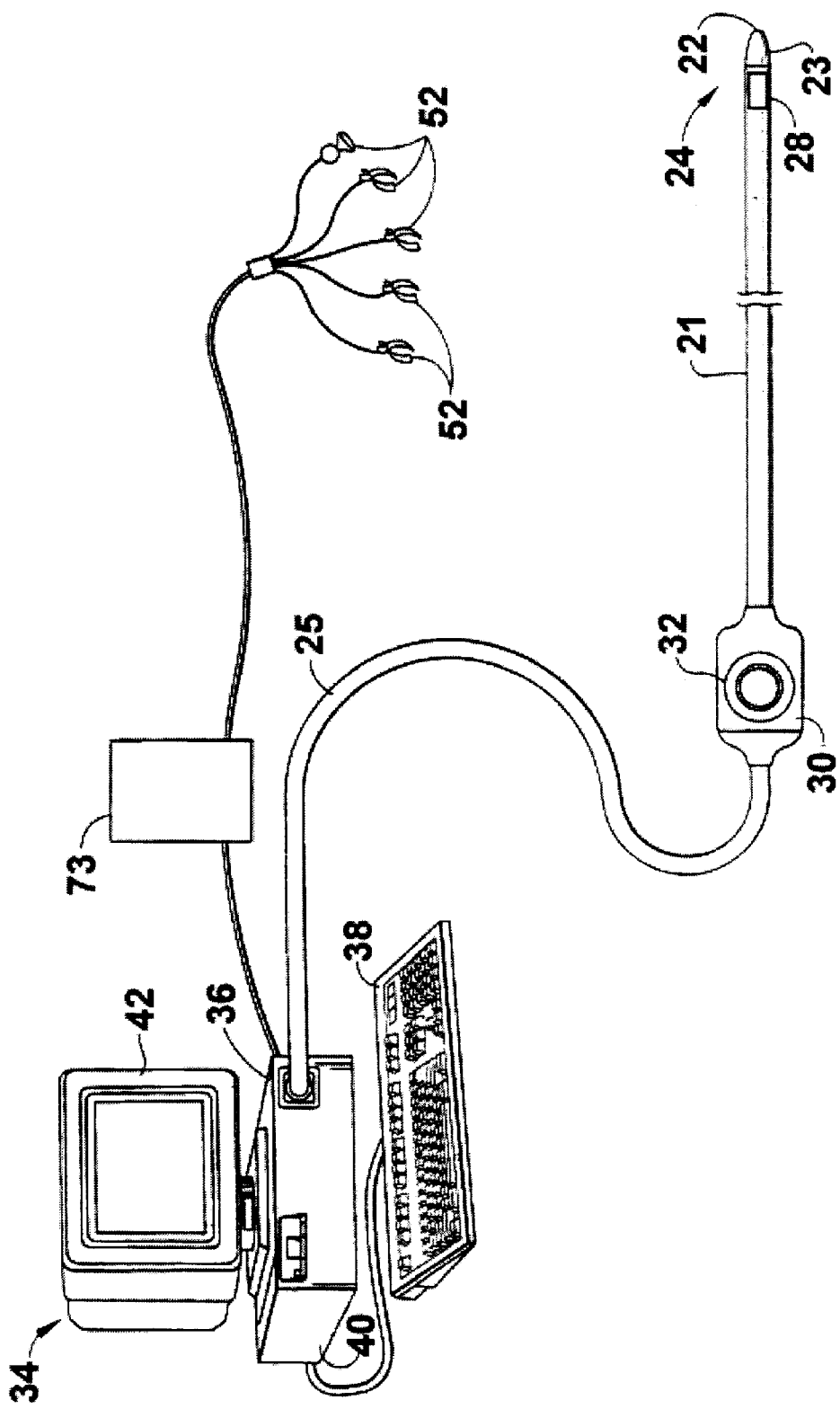
FIG. 9 shows an apparatus for performing the method of the invention.

FIG. 9 shows a preferred apparatus for carrying out the method of the invention. The apparatus comprises catheter 21 for insertion into the human body. Distal end 24 of catheter 21 includes a functional portion 23 for performing diagnostic and/or therapeutic functions, adjacent to distal tip 22. Functional portion 23 preferably comprises electrodes or sensors for performing electrophysiological measurements, as described, for example, in U.S. Pat. No. 5,391,199 or in PCT application WO97/24983, which are incorporated herein by reference. Alternatively or additionally, functional portion 23 may include other diagnostic apparatus for recording parameter values at points within the body. Functional portion 23 may also include therapeutic apparatus as known in the art.

Distal end 22 further preferably includes a sensor 28 that generates signals used to determine the position, and, preferably, the orientation of the catheter within the body. Sensor 28 is preferably adjacent to functional portion 23 in a fixed relation with tip 22. Sensor 28 preferably comprises three coils, such as described in PCT application WO96/05768, which is incorporated herein in its entirety by reference. This sensor enables continuous generation of six dimensions of position and orientation information with respect to externally applied magnetic fields. Alternatively, sensor 28 may comprise other position and/or coordinate sensors as described in U.S. Pat. Nos. 5,391,199, 5,443,489 and PCT application WO94/04938 which are incorporated herein by reference. Further, tip 22 may be coated with an opaque marking material to visualize the tip under an imaging apparatus such as a fluoroscope.

Catheter 21 preferably includes a handle 30, having controls 32 which are used to steer distal end 24 of catheter 21 in a desired direction. Catheter 21 preferably comprises a steering mechanism in distal end 24 as is known in the art to facilitate repositioning of tip 22.

Catheter 21 is coupled via an extension cable 25 to a console 34 which enables the user to observe and regulate the function of catheter 21. Console 34 preferably includes a computer 36, keyboard 38, signal processing circuitry 40, which are typically inside computer 36, and display 42. Signal processing circuits 40 typically receive, amplify, filter and digitize signals from catheter 21, including signals from sensor 28 and functional portion 23, whereupon these digitized signals are used by computer 36 to compute the condition information and the position and/or orientation of catheter tip 22. Alternatively, appropriate circuitry may be associated with catheter 21 itself so that circuits 40 receive signals that are already amplified, filtered and/or digitized. Preferably, computer 36 includes a memory for storing position and condition information. Computer 36 also comprises means for capturing images from an imaging modality either using a video or a DICOM protocol interface. Computer 36 preferably further comprises dedicated graphics hardware for rapidly extracting topographical information and for superposition of topographical images with other images displaying catheter tip 22 in the body. Images containing contour information, images showing the catheter tip 22 and superpositions of these images are displayed on display 42. Preferably, the computer is equipped to receive body surface ECG signals from ECG monitor 73 which is connected to a plurality of ECG body surface leads 52. Alternatively, ECG monitoring may also be conducted directly by circuits 40.

Although this invention has been described in connection with its most preferred embodiments, it will become readily apparent to those reviewing this detailed specification that numerous additional embodiments fall well within the scope and spirit of the claimed invention as set forth in the claims which appear below.

What is claimed is:

1. A method for intracardially surveying a condition of a chamber of a heart of a subject with a catheter having a distal tip, said catheter distal tip having a condition sensor contained therein or proximate thereto, said condition sensor being capable of sensing condition information of said chamber, said method comprising the steps of:

a) acquiring a first image of said chamber, said first image containing topographical information of said chamber;

b) advancing the distal tip of the catheter into the chamber;

c) acquiring a second image comprising a representation of said catheter distal tip in said chamber;

d) extracting topographical information from the image acquired in step (a); superimposing said extracted topographical information with the second image of step (c); and displaying the resultant superimposed image comprising representations of said topographical information and said catheter distal tip;

e) advancing said catheter distal tip to an acquisition point on a wall of said chamber under the guidance of said displayed superimposed image of step (d) and acquiring said condition information at said acquisition point on said chamber wall with said condition sensor, said acquisition point being selected from points on said displayed superimposed image of step (d) proximate said topographical information;

f) repeating step (e) at one or more additional acquisition points, said points being sufficient in number and spacing throughout the chamber to permit the generation of a survey map of said condition in said chamber.

2. The method of claim 1 which further comprises marking the display of the superimposed image to identify the points on the chamber at which said information was acquired.

3. The method of claim 1 wherein said condition is an electrical property.

4. The method of claim 1 wherein said chamber is the left ventricle of the heart.

5. The method of claim 1 wherein said catheter further comprises a position sensor capable of sensing position information.

6. The method of claim 5 wherein said position sensor is an electromagnetic field sensor.

7. The method of claim 5 wherein position information and condition information are acquired at each of said acquisition points.

8. The method of claim 5 which further comprises the step of creating a map of the heart chamber from said condition and position information.

9. The method of claim 1 wherein said first image is a contrast-assisted fluoroscopic image.

10. The method of claim 1 wherein said second image is a fluoroscopic image.

11. The method of claim 1 wherein said second image is acquired using an imaging modality identical to that used in acquiring said first image.

12. The method of claim 11 wherein said first image is a contrast-assisted fluoroscopic image and said second image is a fluoroscopic image.

13. The method of claim 11 wherein said first image and said second image are acquired in a common projection.

14. The method of claim 1 wherein said first image and said second image are acquired from a common projection relative to said subject.

15. The method of claim 1 wherein said extracted topographical information is a contour image of said chamber.

16. The method of claim 1 wherein said topographical information used in step (d) is derived from a single frame of a dynamic, contrast-assisted fluoroscopic image.

17. The method of claim 16 wherein said single frame corresponds to the end-diastole portion of the cardiac cycle.

18. The method of claim 16 wherein said single frame is identified based on its correlation with an electrocardiogram of the subject.

19. A method for intracardially surveying a condition of a chamber of a heart of a subject with a catheter having a distal tip, said catheter distal tip having a condition sensor contained therein or proximate thereto, said condition sensor being capable of sensing condition information of said chamber, said method comprising the steps of:

a) acquiring a first, contrast-assisted fluoroscopic image of said chamber;

b) extracting a contour image of the interior of said chamber from said contrast-assisted fluoroscopic image;

c) advancing the distal tip of the catheter into the chamber;

d) acquiring a second, non-contrast-assisted fluoroscopic image comprising a representation of said catheter distal tip in said chamber, said first image and said second image being acquired from a common projection relative to said subject;

e) displaying a superposition of the contour image of step (b) with the fluoroscopic image of step (d) to generate a superimposed image;

f) advancing said catheter distal tip to an acquisition point on a wall of said chamber under the guidance of said displayed superimposed image of step (e) and acquiring said condition information at said acquisition point on said chamber wall with said condition sensor, said acquisition point being selected from points on said displayed superimposed image of step (e) proximate said contour image;

g) repeating step (f) one or more times at one or more additional acquisition points, said points being sufficient in number and spacing throughout the chamber to permit the generation of a survey map of said condition in said chamber.

20. The method of claim 19 which further comprises marking the display of the superimposed image to identify the points on the chamber at which said information was acquired.

21. The method of claim 19 wherein said condition is an electrical property.

22. The method of claim 19 wherein said chamber is the left ventricle of the heart.

23. The method of claim 19 wherein said catheter further comprises a position sensor capable of sensing position information.

24. The method of claim 23 wherein said position sensor is an electromagnetic field sensor.

25. The method of claim 23 wherein position information and condition information are acquired at each of said acquisition points.

26. The method of claim 23 which further comprises the step of creating a map of the heart chamber from said condition and position information.

27. The method of claim 19 wherein said contour image used in step (e) is derived from a single frame of a dynamic, contrast-assisted fluoroscopic image.

28. The method of claim 27 wherein said single frame corresponds to the end-diastole portion of the cardiac cycle.

29. The method of claim 27 wherein said single frame is identified based on its correlation with an electrocardiogram of the subject.

30. A method for intracardially surveying a condition of a chamber of a heart of a subject with a catheter having a distal tip, said catheter distal tip having a condition sensor contained therein or proximate thereto, said condition sensor being capable of sensing condition information of said chamber, said method comprising the steps of:

a) acquiring a first, contrast-assisted fluoroscopic image of said chamber, said first, contrast-assisted fluoroscopic image being acquired from a first projection relative to said subject;

b) extracting a first contour image of the interior of said chamber from said first contrast-assisted fluoroscopic image;

c) acquiring a second, contrast-assisted fluoroscopic image of said chamber, said second, contrast-assisted fluoroscopic image being acquired from a second projection relative to said subject;

d) extracting a second contour image of the interior of said chamber from said second contrast-assisted fluoroscopic image;

e) advancing the distal tip of the catheter into said chamber;

f) acquiring a first non-contrast-assisted fluoroscopic image comprising a representation of said catheter distal tip in said chamber, said first non-contrast-assisted fluoroscopic image being acquired from said first projection relative to said subject;

g) displaying a superposition of said first contour image of step (b) with said first non-contrast-assisted fluoroscopic image of step (f) to generate a first superimposed image;

h) advancing said catheter distal tip to an acquisition point on a wall of said chamber under the guidance of said displayed superimposed image of step (g) and acquiring said condition information at said acquisition point on said chamber wall with said condition sensor, said acquisition point being selected from points on said first displayed superimposed image of step (g) proximate said first contour image;

i) acquiring a second non-contrast-assisted fluoroscopic image comprising a representation of the catheter distal tip in said chamber, said second non-contrast-assisted fluoroscopic image being acquired from said second projection relative to said subject;

j) displaying a superposition of said second contour image of step (d) with said second non-contrast-assisted fluoroscopic image of step (i) to generate a second superimposed image;

k) advancing said catheter distal tip to an acquisition point on a wall of said chamber under the guidance of said displayed superimposed image of step (j) and acquiring said condition information at said acquisition point on said chamber wall with said condition sensor, said acquisition point being selected from points on said second displayed superimposed image of step (j) proximate said second contour image;

l) repeating steps (h) and (k) at one or more additional acquisition points, said points being sufficient in number and spacing throughout the chamber to permit the generation of a survey map of said condition in said chamber.

31. The method of claim 30 which further comprises marking the display of the superimposed image to identify the points on the chamber at which said information was acquired.

32. The method of claim 30 wherein said condition is an electrical property.

33. The method of claim 30 wherein said chamber is the left ventricle of the heart.

34. The method of claim 30 wherein said catheter further comprises a position sensor capable of sensing position information.

35. The method of claim 34 wherein said position sensor is an electromagnetic field sensor.

36. The method of claim 34 wherein position information and condition information are acquired at each of said acquisition points.

37. The method of claim 34 which further comprises the step of creating a map of the heart chamber from said condition and position information.

38. The method of claim 30 wherein each of said contour images is derived from single frames of dynamic, contrast-assisted fluoroscopic images.

39. The method of claim 38 wherein said single frames correspond to the end-diastole portion of the cardiac cycle.

40. The method of claim 38 wherein said single frame is identified based on its correlation with an electrocardiogram of the subject.

41. The method of claim 30 wherein all condition information acquired at acquisition points from one of the displayed superimposed images is acquired before the acquisition of condition information acquired at acquisition points from the other displayed superimposed image.

42. Apparatus for intracardially surveying a condition of a chamber of a heart of a subject, said apparatus comprising:

a) a catheter for acquiring condition information at a number of points in said chamber, said catheter having a distal tip and a sensor contained therein, said sensor capable of sensing said condition information, said points being sufficient in number and spacing throughout the chamber to permit the generation of a survey map of said condition in said chamber;

b) means for extracting topographical information from a first image of said chamber;

c) means for superimposing and displaying a superposition of said topographical information extracted from said first image with a second image, said second image comprising a representation of said catheter distal tip in said chamber; said superposition being used to guide said catheter distal tip to the wall of said chamber.

43. The apparatus of claim 42 further comprising means for marking said displayed superposition to identify the points in the chamber at which said information was acquired.

44. The apparatus of claim 42 wherein said topographical information comprises a contour of said chamber of said heart.

45. The apparatus of claim 42 wherein said condition sensor is an electrical sensor.

46. The apparatus of claim 42 wherein said catheter further comprises a position sensor.

47. The apparatus of claim 46 wherein said position sensor is an electromagnetic position sensor.

* * * * *